US012545928B2

(12) United States Patent
Wnuk et al.

(10) Patent No.: US 12,545,928 B2
(45) Date of Patent: Feb. 10, 2026

(54) MACHINE METHODS TO DETERMINE NEOEPITOPE PAYLOAD TOXICITY

(71) Applicants: Nantomics, LLC, Culver City, CA (US); NantBio, Inc., Culver City, CA (US)

(72) Inventors: Kamil Wnuk, Playa Vista, CA (US); Lise Geissert, Culver City, CA (US); Jeremi Sudol, Culver City, CA (US); Charles Vaske, Culver City, CA (US); Stephen Charles Benz, Santa Cruz, CA (US); Connie Tsai, Culver City, CA (US); Kayvan Niazi, Culver City, CA (US); Christopher W. Szeto, Culver City, CA (US)

(73) Assignees: Nantomics, LLC, Culver City, CA (US); NantBio, Inc., Culver City, CA (US)

( * ) Notice: Subject to any disclaimer, the term of this patent is extended or adjusted under 35 U.S.C. 154(b) by 1039 days.

(21) Appl. No.: 17/633,876

(22) PCT Filed: Jul. 24, 2020

(86) PCT No.: PCT/US2020/043548
§ 371 (c)(1),
(2) Date: Feb. 8, 2022

(87) PCT Pub. No.: WO2021/030030
PCT Pub. Date: Feb. 18, 2021

(65) Prior Publication Data

US 2022/0403413 A1 Dec. 22, 2022

Related U.S. Application Data

(60) Provisional application No. 62/885,089, filed on Aug. 9, 2019.

(51) Int. Cl.
*C12N 15/86* (2006.01)

(52) U.S. Cl.
CPC .... *C12N 15/86* (2013.01); *C12N 2710/10343* (2013.01)

(58) Field of Classification Search
CPC ...................... C12N 15/86; C12N 2710/10343
See application file for complete search history.

(56) References Cited

U.S. PATENT DOCUMENTS

| | | | | |
|---|---|---|---|---|
| 11,557,375 | B2 * | 1/2023 | Sudol | G16B 40/20 |
| 12,270,813 | B2 * | 4/2025 | Sahin | A61K 39/0011 |
| 2022/0267798 | A1 * | 8/2022 | Feschenko | C07K 14/475 |
| 2023/0274796 | A1 * | 8/2023 | Sudol | G16B 40/20 702/19 |

FOREIGN PATENT DOCUMENTS

| | | | |
|---|---|---|---|
| CN | 106636164 | A | 5/2017 |
| WO | 2009/006479 | A3 | 1/2009 |
| WO | 2016/172722 | A1 | 10/2016 |
| WO | 2017/136748 | A1 | 8/2017 |
| WO | 2017/222619 | A3 | 12/2017 |
| WO | 2019/074907 | A1 | 4/2019 |
| WO | 2019/147921 | A1 | 8/2019 |
| WO | 2019/236842 | A1 | 12/2019 |
| WO | 2020/028862 | A1 | 2/2020 |

OTHER PUBLICATIONS

Murray et al,"Diverse and Specific Gene Expression Responses to Stresses in Cultured Human Cells", Molecular Biology of the Cell, vol. 15, 2361-2374, May 2004.
Amalfitano et al., "Production and Characterization of Improved Adenovirus Vectors with the E1, E2b, and E3 Genes Deleted", Journal of Virology, vol. 72, No. 2, Feb. 1998, pp. 926-933.
Gómez-Bombarelli et al., "Automatic Chemical Design Using a Data-Driven Continuous Representation of Molecules", URL: https://arxiv.org/pdf/1610.02415.pdf, Dec. 5, 2017, pp. 1-26.
Gubin et al., "Tumor neoantigens: building a framework for personalized cancer immunotherapy", The Journal of Clinical Investigation, Review Series: Cancer Immunotherapy, vol. 125, No. 9, Sep. 2015, pp. 3413-3421.
Gupta et al., "In Silico Approach for Predicting Toxicity of Peptides and Proteins", PLOS | One vol. 8, No. 9, e73957, Sep. 2013, pp. 1-10.
Schumacher et al., "Neoantigens in cancer immunotherapy", Science, Reviews, vol. 348, No. 6230, Apr. 3, 2015, pp. 69-74.
Sanborn, John Zachary, "Panbam: Bambam Across Multiple Organisms In Parallel", U.S. Appl. No. 62/714,570, filed Aug. 3, 2018, 26 pages.
Sanborn et al., "Difference-Based Genomic Identity Scores", U.S. Appl. No. 62/681,800, filed Jun. 7, 2018, 52 pages.
Wu et al., "TSNAdb: A Database for Tumor-specific Neoantigens from Immunogenomics Data Analysis", Elsevier, Genomics Proteomics Bioinformatics, vol. 16, Sep. 15, 2018, pp. 276-282.
Zhou et al., "TSNAD: an integrated software for cancer somatic mutation and tumour-specific neoantigen detection", Royal Society Open Science, vol. 4, No. 4, Article 170050, Apr. 5, 2017, pp. 1-12.
International Search Report and Written Opinion received for PCT Application Serial No. PCT/US2020/043548 dated Nov. 11, 2020, 8 pages.

(Continued)

*Primary Examiner* — Janet L Andres
*Assistant Examiner* — Carey Alexander Stuart
(74) *Attorney, Agent, or Firm* — Umberg/Zipser, LLP; Martin Fessenmaier; Priti Phukan

(57) ABSTRACT

Systems and methods are presented that allow for determination and prediction of payload toxicity in therapeutic viruses. Contemplated methods of determining payload toxicity of an expressed polypeptide in a cell may comprise the steps of generating or procuring a plurality of expression vectors, each containing a different recombinant nucleic acid sequence that encodes a corresponding recombinant polypeptide; expressing the recombinant nucleic acid sequence in a plurality of host cells while culturing the host cells; sequencing the plurality of expression vectors after culturing the host cells; and correlating at least portions of the recombinant nucleic acid sequence with a toxicity measure.

20 Claims, 4 Drawing Sheets

Specification includes a Sequence Listing.

(56) References Cited

OTHER PUBLICATIONS

Wu et al., Machine Learning Based Toxicity Prediction: From Chemical Structural Description to Transcriptome Analysis, International Journal of Molecular Sciences, vol. 19, No. 2358, Aug. 10, 2018, pp. 1-20.

International Preliminary Report on Patentability received for PCT Application Serial No. PCT/US2020/043548 dated Feb. 17, 2022, 6 pages.

Extended European Search Report received for EP Patent Application Serial No. 20852869.5 dated Aug. 3, 2023, 7 pages.

Wirth et al., "Neoantigen Targeting?Dawn of a New Era in Cancer Immunotherapy?", Frontiers in Immunology, vol. 8, Dec. 19, 2017, pp. 1-16.

English Translation of First Office Action received in Chinese Patent Application No. 202080052457.0 dated Jun. 6, 2025, 11 pages.

* cited by examiner

| Vectors | Toxicity |
|---|---|
| pShuttle-CMV (empty vector) | No |
| pShuttle-CMV-LMP1 | Yes |
| pShuttle-CMV-LMP1/IPS1 | Yes |
| pShuttle-CMV-B16-Neo1 | No |
| pShuttle-CMV-B16-Neo2 | No |
| pShuttle-CMV-GFP | No |

MACHINE METHODS TO DETERMINE NEOEPITOPE PAYLOAD TOXICITY

This application claims priority to our U.S. provisional patent application with the Ser. No. 62/885,089 which was filed Aug. 9, 2019, which is incorporated by reference herein in its entirety.

SEQUENCE LISTING

The content of the ASCII text file of the sequence listing named 102402.0071PCT_ST25, which is 1,686 bytes in size was created on Jul. 23, 2019 and electronically submitted via EFS-Web along with the present application, and is incorporated by reference in its entirety.

FIELD OF THE INVENTION

The present disclosure relates to various systems and methods to determine and/or avoid toxicity of recombinant virus payload in a host organism, especially as it relates to toxicity of neoepitopes in host cells for production of therapeutic viruses.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Generation of recombinant therapeutic viral vaccines has become an increasingly attractive strategy for treatment of various diseases, and particularly for viruses used to prepare a cancer vaccine. Unfortunately, while identification and selection of potentially immunogenic neoepitope sequences has made rapid progress, toxicity of the expressed neoepitope(s) will in most cases only become evident after generation of the therapeutic recombinant virus and start of large scale virus production. To avoid at least some of the disadvantages associated with potential payload toxicity, expression of the recombinant payload can be suppressed in production cells various manners as is described in PCT/US2018/054982. Such approach will advantageously achieve suitably high viral titers in a production environment. However, once patient cells are infected with the recombinant therapeutic virus, payload toxicity effects in the patient's cells may reduce expression of the neoepitope(s). In other known methods, toxicity of a protein can be determined using a predictive algorithm that identifies potentially toxic sequences in a protein based on known toxicities of known proteins (see *PLoS ONE* 8(9): e73957). While conceptually attractive, such method is based on naturally occurring polypeptides and will typically not be applicable to artificial sequence constructs (e.g., encoding multiple neoepitope sequences that are connected by linker sequences and optionally contain trafficking signals).

Thus, even though various methods of reducing toxic effects of a recombinant viral payload are known in the art, all or almost all of them suffer from various disadvantages. Consequently, there is a need to provide improved compositions and methods that allow production of recombinant therapeutic viruses with reduced toxicity.

SUMMARY OF THE INVENTION

Various systems and methods are presented that allow determination of payload toxicity in recombinant therapeutic viruses. In one aspect of the inventive subject matter, the inventors contemplate a method of determining payload toxicity of an expressed polypeptide in a cell that includes a step of generating or procuring a plurality of expression vectors, each containing a different recombinant nucleic acid sequence that encodes a corresponding recombinant polypeptide, a further step of expressing the recombinant nucleic acid sequence in a plurality of host cells while culturing the host cells, another step of sequencing the plurality of expression vectors after culturing the host cells, and a step of correlating at least portions of the recombinant nucleic acid sequence with a toxicity measure.

In at least some embodiments, the expression vectors are viral expression vectors, and especially recombinant genomes of respective therapeutic viruses. It is further contemplated that the recombinant polypeptide is a polytope comprising a plurality of neoantigens, typically with the neoantigens being separated by a linker peptide. Preferably, the neoantigens have a length of between 8-50 amino acids, and/or the polytope includes at least 200 amino acids.

It should be further appreciated that the recombinant nucleic acid sequence can be monoclonally or polyclonally expressed in the plurality of host cells. Therefore, the plurality of expression vectors can be individually sequenced, or sequenced in a mixture of expression vectors. In further aspects of contemplated methods, the toxicity measure is observed in the host cells (e.g., as cell death, cell stress, reduced cell division, and/or reduced virus production), while in other aspects the toxicity measure is observed in the recombinant nucleic acid sequence of the virus (e.g., as nonsense mutation, missense mutation, and/or a deletion).

Additionally, it is contemplated that the step of correlating uses machine learning, which may employ various classifiers such as a linear classifier, an NMF-based classifier, a graphical-based classifier, a tree-based classifier, a Bayesian-based classifier, a rules-based classifier, a net-based classifier, or a kNN classifier. Alternatively, the machine learning may also use an autoencoder. Where desired, the machine learning may further use a secondary aspect of the recombinant polypeptide, such as a folding pattern of the polypeptide, a secondary structure of the polypeptide, a polarity domain, a charged domain, a hydrophobic domain, a hydrophilic domain, and/or aggregation of the polypeptide.

Various objects, features, aspects, and advantages will become more apparent from the following detailed description of preferred embodiments, along with the accompanying drawing in which like numerals represent like components.

DETAILED DESCRIPTION

Figure 1:
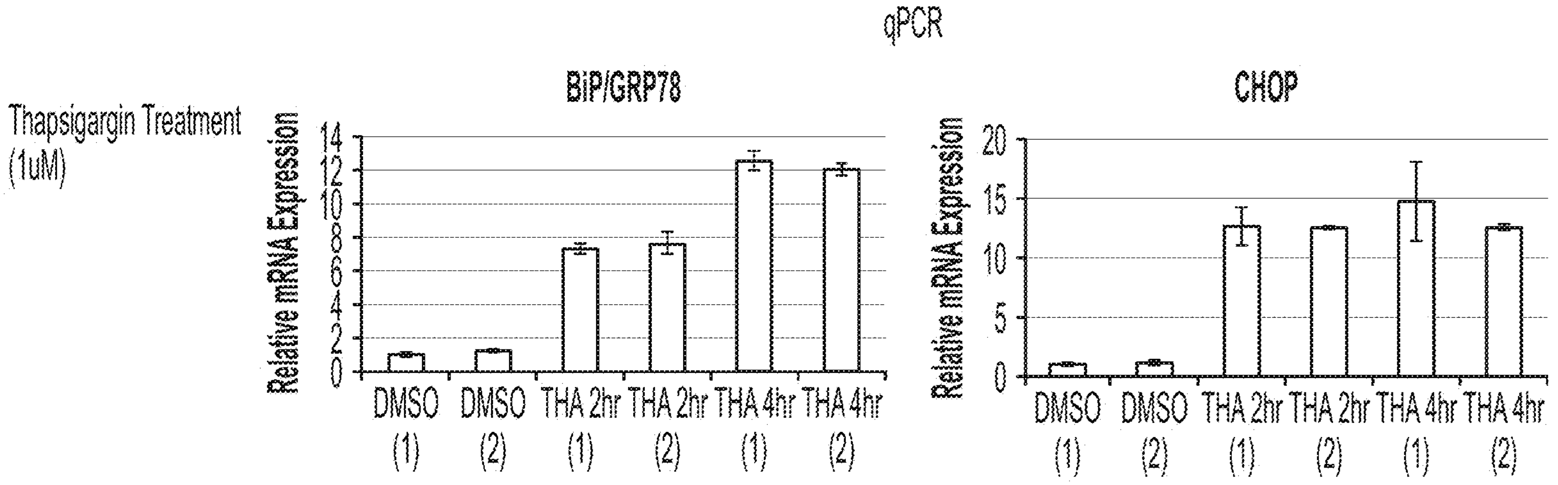
FIG. 1 depicts exemplary results for determination of cell stress by various payloads as determined by qPCR.
Figure 1:
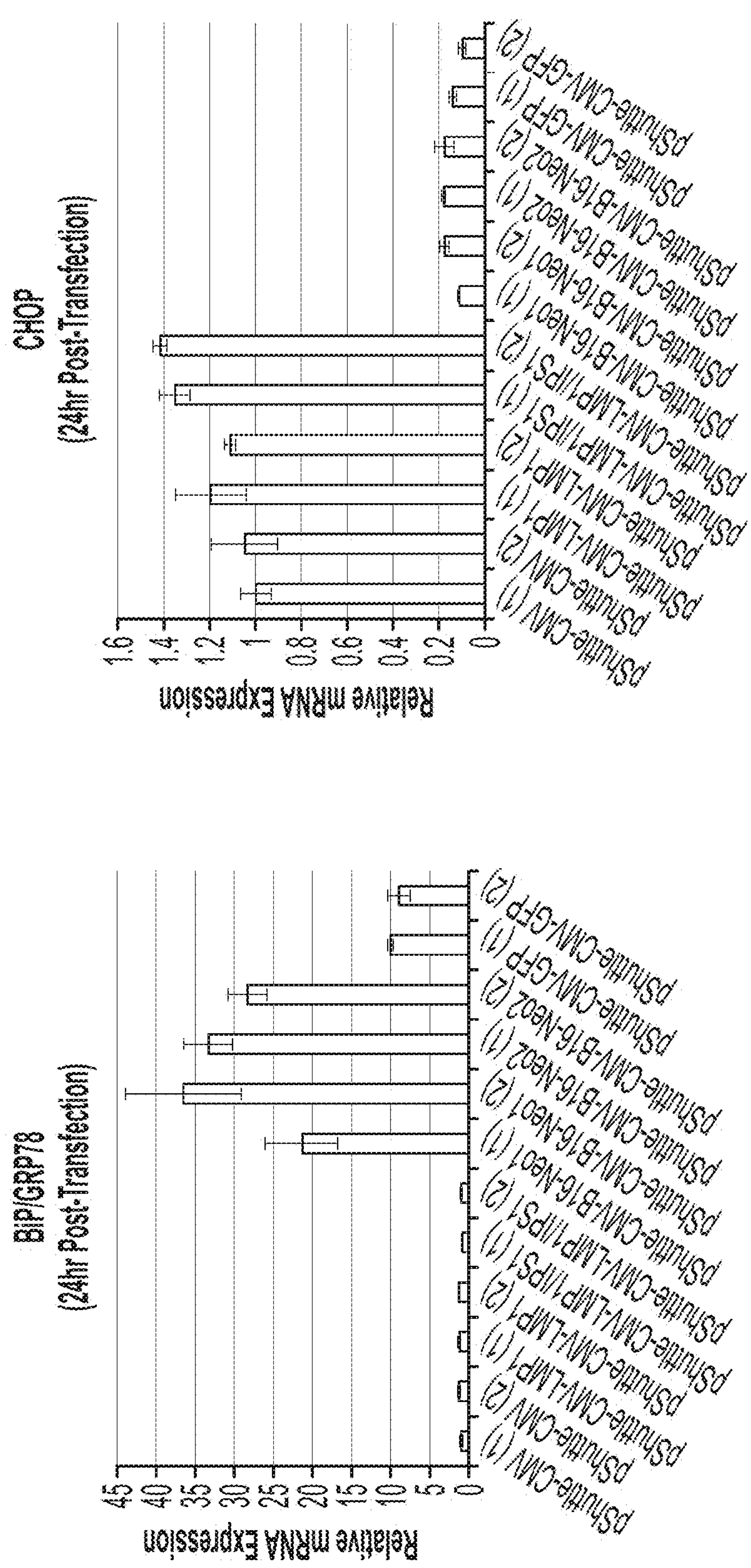

The inventors have now discovered that a rational-based approach to determine payload toxicity can be employed in which a number of payload sequences of respective viruses are correlated with one or more toxicity measures in a host cell producing the virus, preferably using a machine learning approach.

To that end, and in a more general aspect of the inventive subject matter, the inventors contemplate that multiple viral payloads are expressed in (respective cultures of) the same host cell line to generate viral progeny to at least some degree. Depending on the type of toxicity measure (e.g., cell stress, apoptosis, host cell growth retardation, mutations (e.g., non-sense, missense) in payload, reduction of viral titer at predetermined culture time, increased production time for target titer, etc.) the cells and/or virus cultures are then analyzed. Of course, it should be appreciated that analysis can be performed on an individual/clonal basis, or massively parallel using a mixed (virus and/or host cell) clonal population. Analysis results for the payload sequences are then processed using machine learning that correlates one or more toxicity measures with one or more payload sequence parameters (e.g., charge and/or hydrophobicity pattern, specific amino acid usage or patterns, structural motifs or folding patterns, etc.). Most typically, the payload sequence parameters are analyzed across more than one neoepitope within a single payload, such as a polytope or a single translational unit.

Procurement or generation of clonal diversity for the plurality of viruses with respective payload can be based on various materials, and especially includes patient neoantigen sequences that can be obtained from various publically available sources (e.g., *Genomics Proteomics Bioinformatics* 16 (2018) 276-282; or WO 2016/172722), or de novo determined neoantigen sequences derived from unpublished patient or TCGA data using various methods known in the art (see e.g., *Science.* 2015; 348:69-74; or *J Clin Invest.* 2015; 125:3413-3421; or *R Soc Open Sci.* 2017; 4:170050; or *R Soc Open Sci.* 2017; 4:170050). Such data may be further refined to predict MHC binding using various bioinformatics tools, and a particularly well known tool is NetMHC 4.0.

Most typically, the neoantigens (also referred to as neoepitopes) in contemplated methods are arranged in a recombinant polytope sequence, preferably with intervening flexible linker sequences. Moreover, contemplated polytope sequences may further include trafficking sequences to direct the recombinant protein towards a specific subcellular location (e.g., cytoplasm, lysosome, endosome, etc.). Where desired, ubiquitination signals may also be included. Exemplary suitable sequence arrangements are described in WO 2017/222619. In this context, it should be appreciated that where neoantigens are present and expressed in a polytope, toxicity measures may relate to individual neoantigens, or to a polypeptide that includes more than one neoantigen. Viewed form a different perspective, it is contemplated that two or more otherwise non-toxic neoantigens can have toxic effects on a host cell where such neoantigens form a polytope. Such compound toxicity is not detectable where individual antigens are analyzed per se. As will be readily appreciated, the neoantigen, and more preferably the polytope containing the neoantigens will be expressed from an expression vector, which may further include additional functionalities (e.g., co-stimulatory molecules, cytokines, ALT-803, T×M-type molecules, checkpoint inhibitors, etc.).

While most expression vectors are deemed suitable for use herein, it is particularly preferred that the neoantigen or polytope is expressed from a recombinant viral genome using suitable control elements know in the art. Use of such recombinant viruses in the methods presented herein will provide at least two advantages, including downstream use of such viruses in the production of a therapeutic virus, and assessment of potential toxicity in the context of viral reproduction. Thus, the host cells used for assessment of toxicity will have suitable configuration to allow for viral infection. For example, where the recombinant virus is an AdV adenovirus with deleted E2b protein, contemplated host cells will express (natively or from a recombinant nucleic acid) a CXADR (coxsackie virus and adenovirus receptor). Exemplary host cells for adenovirus-based systems include E.C7 cells (commercially available from Etubics) and those described in WO 2009/006479 and WO 2017/136748. Still further contemplated viruses suitable for use as recombinant expression vectors for therapeutic antigens include various adenoviruses, adeno-associated viruses, alphaviruses, herpes viruses, lentiviruses, etc. However, adenoviruses are particularly preferred. Moreover, it is further preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933).

With respect to the toxicity of the payload it should be appreciated that toxicity may affect the host (i.e., infected or otherwise transfected) cell as well as the virus in a variety of ways. For example, the expressed polytope or portion thereof (e.g., one or more neoantigen or neoantigen-linker portions) may be immediately toxic to a cell and interfere with metabolism, cell division, or cell signaling. On the other hand, the expressed polytope or portion thereof may also be indirectly toxic and may affect various intracellular processes and structures such as transcription, translation, protein turnover, energy production, as well as membrane integrity of various organelles, nuclear and/or mitochondrial stability, etc. Still further, it should be noted that the expressed polytope or portion thereof may exert adverse selective pressure on the cell and may so indirectly lead to mutations in the nucleic acid encoding the expressed polytope or portion thereof. Consequently, toxicity may also result in production of mutated recombinant (viral) nucleic acids in which the mutated nucleic acid will have premature stop codons and/or missense mutations that reduce the adverse selective pressure. Therefore, and viewed form a different perspective, toxicity may result in cell death (typically via apoptosis or necrosis), reduced or otherwise impaired cell division, cellular stress (and typically associated reduced metabolism and (viral) replication), mutations in the recombinant payload, reduction of the viral titer at predetermined culture time, and/or an increase in production time for predetermined target titer.

In still further contemplated aspects, toxicity may also be determined in vivo using various proxy measures in a host cell that can be directly or indirectly observed. For example, one or more biomarkers may be quantified in the host cell that correlate with apoptosis or cell stress. As shown in more detail below, upregulation of ER stress markers (e.g., BiP/Grp78, XBP-1 cleavage) may be measured, as well as repression CHOP-induced apoptosis that correlates with survival of host cells. Additionally it should be recognized that cellular stress may also be identified and even quantified using a compunomics approach in which a stress-related transcription factor (e.g., XBP-1) activates expression of a recombinant marker molecule (e.g., GFP).

Therefore, depending on the type of toxicity observed, expression of the payload in the host cell may be done monoclonally or in mixed culture. For example, where the payload is a polytope that includes actual patient neoantigens and where the payload is already present in a therapeutic virus, expression of the payload is typically performed in a monoclonal manner (i.e., host cells are infected with a single clone (genotype) of therapeutic virus and the so infected cells are cultured to a desired cell density and/or viral titer. On the other hand, where the payload is an exploratory payload (i.e., not used in a therapeutic virus), multiple recombinant viruses with a diversity library that is based on the same polytope can be used to transfect a plurality of host cells in a polyclonal virus culture as is described in more detail below.

Regardless of the type of toxicity of the payload, sequence analysis of the recombinant nucleic acid of the virus (or other expression vector) can be done in numerous manners well known in the art, and the type of payload and/or observed toxicity will at least in part determine the type of sequencing employed. For example, where the payload is present in a therapeutic virus and where the virus is propagated in a monoclonal manner, sequence analysis can be performed from a virus isolate. On the other hand, where a plurality of viruses is propagated in a polyclonal virus culture, sequencing can be performed en-masse using collective nucleic acids without prior clonal selection of individual viruses. Of course, it should be appreciated that all sequencing approaches are preferably automated sequencing methods that allow for high data throughput such as Next-Gen/Illumina sequencing and other massively parallel sequencing methods. In this context, it should be recognized that where sequencing is performed on mixed viral nucleic acids (e.g., such as those obtained from polyclonal viral culture), sequence analysis will employ methods that can provide 'allele fractions' or 'purity/mutant fractions' for a specific base position in the nucleic acid that encodes the neoantigen and/or neoepitope. Exemplary suitable methods are described in our co-pending US Provisional applications with the Ser. Nos. 62/714,570 (PANBAM: BAMBAM Across Multiple Organisms In Parallel) and 62/681,800 (Difference-Based Genomic Identity Scores), both incorporated by reference herein.

Moreover, it should be noted that the sequence analysis can be performed at multiple time over the tie of cell culture to so help identify the incidence and fraction of mutations (in one or all viral genomes) over time. Consequently, it should be appreciated that the sequence analysis will provide not just qualitative information of mutations in a virus or viral population, but also quantitative and temporal information of mutations in the virus or viral population. For example, where the cell culture is used to propagate a monoclonal virus population (e.g., for a therapeutic virus), virus samples may be withdrawn at predetermined intervals to reveal after sequencing the occurrence and fraction of virus mutants over time. On the other hand, where the cell culture is used to propagate a polyclonal virus population (e.g., based on a library of mutant sequences), virus samples may be withdrawn at predetermined intervals to reveal after sequencing the dynamic chances of selected virus mutants over time.

Depending on the observed toxicity measure and type of mutation, various machine learning algorithms can be employed to correlate one or more motifs in the payload sequence (e.g., domains, one or more amino acids in specific positions, sequence length, amino acid composition, predicted folding, etc.) with the observed toxicity. As will be readily appreciated, numerous types of classifiers can be selected, and suitable classifiers include one or more of a linear classifier, an NMF-based classifier, a graphical-based classifier, a tree-based classifier, a Bayesian-based classifier, a rules-based classifier, a net-based classifier, a kNN classifier, or other type of classifier. More specific examples include NMFpredictor (linear), SVMlight (linear), SVMlight first order polynomial kernel (degree-d polynomial), SVMlight second order polynomial kernel (degree-d polynomial), WEKA SMO (linear), WEKA j48 trees (trees-based), WEKA hyper pipes (distribution-based), WEKA random forests (trees-based), WEKA naive Bayes (probabilistic/bayes), WEKA JRip (rules-based), glmnet lasso (sparse linear), glmnet ridge regression (sparse linear), glmnet elastic nets (sparse linear), artificial neural networks (e.g., ANN, RNN, CNN, etc.) among others. Additional sources for prediction model templates 140 include Microsoft's CNTK (see URL github.com/Microsoft/cntk), TensorFlow (see URL tensorflow.com), PyBrain (see URL pybrain.org), or other sources.

Alternatively, and especially where relatively low numbers of toxicity examples are available, the inventors contemplate use of encoders that were trained on the MHC-peptide binding problem to get representations of the example neoepitopes, and from there train a toxicity classifier specific to the production cell line. While at least initially such approach may not generalize well and make mistakes, human supervision may be employed to flag examples whose predicted toxicity turns out to be incorrect and to add them to the training set. Using such intervention, the system accuracy should improve quickly and eventually generalize well.

Upon reaching a data threshold, machine learning can also use an approach in which autoencoders are employed (see e.g., arXiv:1610.02415v3) that enable transformation of polytopes into a continuous latent space, and then back from latent space to poly-topes. To constrain the structure of the latent representation, predictors of various molecule properties can be jointly trained. One benefit that any encoder/decoder pair allows is the ability to perturb a point in the latent space or interpolate between points followed by passing the new representation through the decoder, in this case to sample a possible resulting polytope. But because the latent representation was learned jointly with the task of predicting polytope properties, it is noted that the latent space also becomes more amenable to optimization of a polytope for desired properties. In other words, one can use gradients from trained predictors to shift a point in the latent space such that it will lead to more or less of a desired property.

With respect to toxicity and MHC binding work, it is noted that if one of the jointly trained properties being predicted from a latent representation of peptides was toxic to a certain production cell then, once we have a candidate neoepitope, one can follow the gradient in the latent space to minimize toxicity while trying to retain fidelity to the original candidate. If from that same latent space representing the peptide one also predicts binding to different MHC alleles, then in theory one would be able to optimize in parallel for maximizing predicted binding in alleles of interest and minimizing toxicity to select production methods.

Note that there could be multiple parallel predictions made about toxicities across multiple cell lines or production processes (assuming there was sufficient data to train for each). Further, when optimizing in consideration of toxicity, one or more production method toxicities could be used as constraints. Furthermore, it should be noted that the types of allowable peptide modifications are only restricted by design choice of model used for encoder/decoder. Thus models that can handle variable lengths in both inputs and outputs, such as fully convolutional nets or RNNs, can allow for changes in peptide length as well as amino acid substitutions.

Therefore, it should be appreciated that on the basis of observed toxicity and the knowledge of the payload sequence, toxicity parameters (and especially a toxicity threshold) can be learned. Once established, known payloads can be eliminated or reconfigured to reduce or entirely avoid toxicity to the host cell.

EXAMPLES

Determination of toxicity and associated observed mutations in viral payload: In the following example, payloads were constructed and cloned into an AdV virus with deleted E2b gene and the virus was propagated in E.C7 cells. Toxicities were observed and genetic changes in the viral payload detected as described. Polytopes varied in length between about 1.1 Kb and 11.2 Kb, and further include ubiquitination signals, co-stimulatory molecules, and trafficking signals as indicated in the Table below.

| Name of Neoepitope Target | Shorthand Name | Results due to Possible Sequence Toxicity |
|---|---|---|
| (1.1) Kb epitopes-UBQ-GP2A-(11.2) IAb epitopes-CD1c | 1-11. | Deletion of nucleotides 816-3018 |
| (1.1) Kb epitopes-UBQ-GP2A-(11.2) IAb epitopes-CD1c-m41BBL | 1-11bb | 2 point mutations, one resulting in early stop codon. Mutations g970a and g1783t (stop codon) |
| (4.2)KbCyto-P2A-(10.1)IAbCD1a-T2A-mOX40L | 4-10ox | Point mutation g1111t - early stop codon |
| (1.1)KbUBQ-P2A-(10.1)IAbCD1a-T2A-m41BBL-P2A-mOX40L | 1-10bbox | Point mutation c2533t - early stop codon |
| (4.2)KbCyto-P2A-(9.2)IAbLAMP1-T2A-m41BBL-P2A-mOX40L | 4-9bbox | Point mutation c1018t - early stop codon |
| (1.1)KbUBQ-GP2A-(9.2)IAbLAMP1 | 1-9. | Deletion of nucleotides 1-677 |
| (4.2)KbCyto-GP2A-(9.2)IAbLAMP1 | 4-9 | Nucleotides 2919 through 3089 deleted and foreign DNA inserted in this position |
| (9.2) IAb-LAMP1-IRES-4F10 | 9.2-4F10 | Nucleotides 1700 through 3482 deleted |
| (11.2) I-Ab epitope-cd1c (sorting endosome)-IRES-4F10 | 11.2-4F10 | Very slow production of virus. 9 passages were carried out to produce lower titer yields |
| (1.1) Kb epitope-UBQ-IRES-4F10 | 1.1-4F10 | Slow production of virus. 7 passages were carried out to produce lower titer yields |
| (4.2) Kb epitopes-Cyto-GP2A-(10.1) IAb epitopes-CD1a | 1-10 | Moderately slow production of virus. 7 passages needed for higher titer yields |
| (1.1) Kb epitopes-UBQ-GP2A-(10.1) IAb epitopes-CD1a-m41BBL | 1-10bb | Moderately slow production of virus. 7 passages needed for higher titer yields |
| (4.2) Kb epitopes-Cyto-GP2A-(10.1) IAb epitopes-CD1a-m41BBL | 4-10bb | Moderately slow production of virus. 7 passages needed for higher titer yields |

As can be seen from the table, toxic payloads resulted in deletions, point mutations, and nonsense mutations in the viral payload, as well as in slower production of virus particles to reach a predetermined titer. Moreover, it should be noted that toxicity can be correlated with the payload sequence and attendant changes in the payload sequence.

Model biomarkers to detect toxicity of a payload: In this exemplary system, E.C7 cells were treated with 1 μM Thapsigargin or transfected with pShuttle plasmids using Lipofectamine 3000. Reverse transcription and cDNA synthesis was performed using RNeasy (Qiagen) and High capacity cDNA synthesis kit (Applied Biosystems) according to manufacturer's protocol. Relative mRNA expression was calculated by normalizing to samples to internal control RPL19. Expression was quantified using qPCR after rtPCR using the following primers:

| Gene | Species | For | Rev | Product | Reference |
|---|---|---|---|---|---|
| RPL19 | Human | ATGTATCACAGCCTGTACCTG (SEQ ID NO: 1) | TTCTTGGTCTCTTCCTCCTTG (SEQ ID NO: 2) | 233 | Hiramatsu, 2011 |

-continued

| Gene | Species | For | Rev | Product | Reference |
|---|---|---|---|---|---|
| BiP/GRP78 | Human | CGGGCAAAGATGTCAGGAAAG (SEQ ID NO: 3) | TTCTGGACGGGCTTCATAGTAGAC (SEQ ID NO: 4) | 211 | Hiramatsu, 2011 |
| CHOP | Human | ACCAAGGGAGAACCAGGAAACG (SEQ ID NO: 5) | TCACCATTCGGTCAATCAGAGC (SEQ ID NO: 6) | 201 | Hiramatsu, 2011 |
| XBP1 | Human | TTACGAGAGAAAACTCATGGC (SEQ ID NO: 7) | GGGTCCAAGTTGTCCAGAATGC (SEQ ID NO: 8) | s-257, u-283 | Hiramatsu, 2011 |

Figure 2:
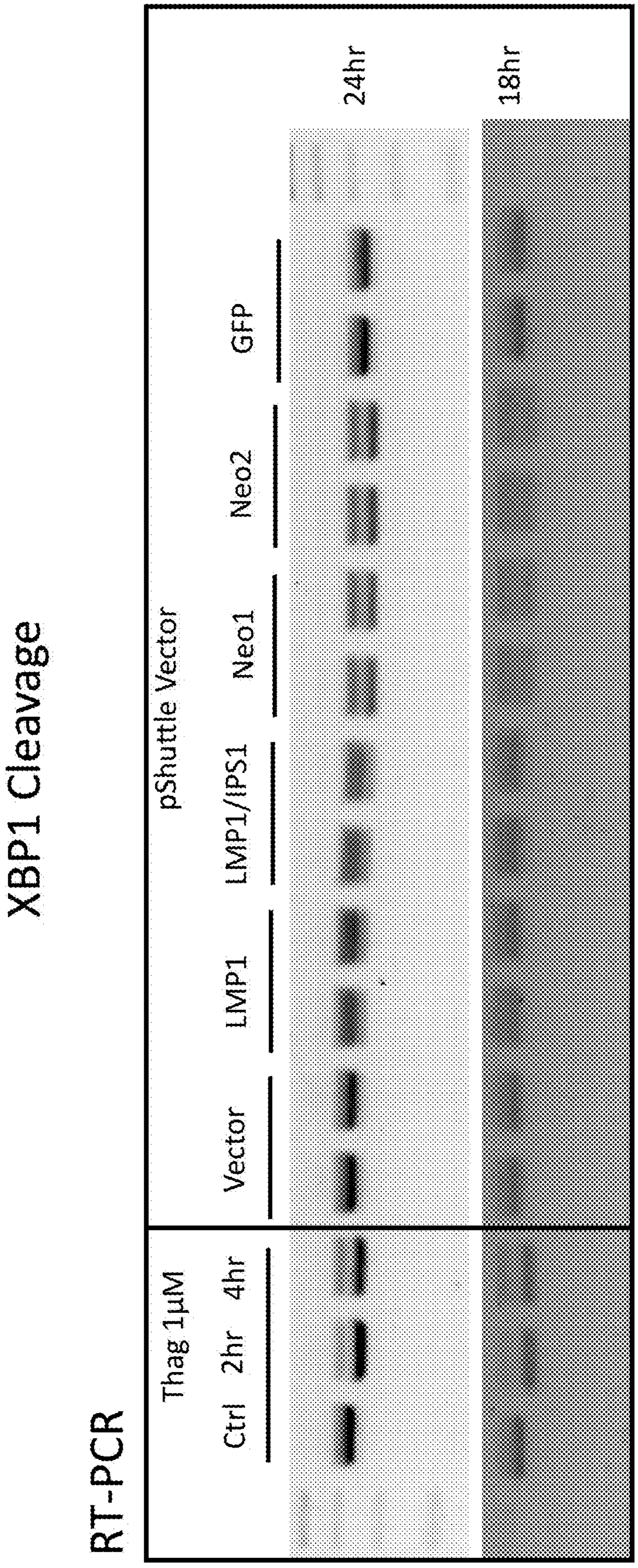
FIG. 2 depicts exemplary results for determination of cell stress by various payloads as determined by XBP1 cleavage.
Figure 3:
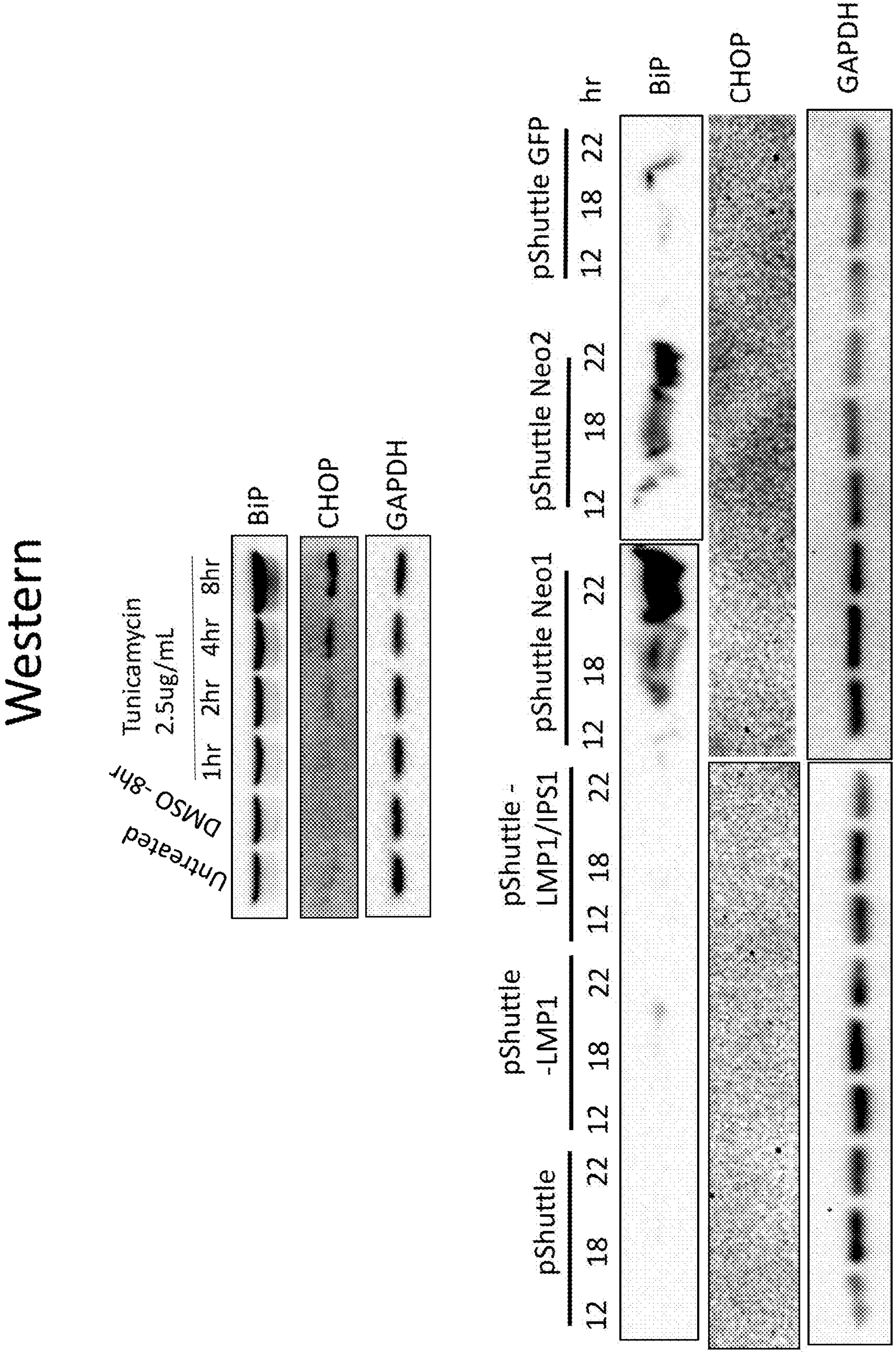
FIG. 3 depicts exemplary results for determination of cell stress by various payloads as determined by Western Blot.

FIGS. 1-3 depict exemplary results for such model system. More specifically, FIG. 1 shows selected biomarkers upon treatment of the cells with Thapsigargin as positive control (upper panels) and exemplary toxicity results with expression vectors carrying payload as indicated (lower panel). FIG. 2 depicts exemplary results for XBP1 cleavage, and FIG. 3 depicts results for a Western blot. Here, E.C7 cells were treated with 1 μg/mL Tunicamycin or transfected with pShuttle plasmids using Lipofectamine 3000. Total protein lysate was extracted using RIPA buffer (20 mM Tris-HCl pH 7.5, 150 mM NaCl, 1 mM $Na_2EDTA$ 1 mM EGTA 1% NP-40, 1% sodium deoxycholate) supplemented with protease inhibitors. Lysate was probed with BiP (CST #3177), CHOP (CST #2895) and GAPDH (CST #2118) antibodies at 1:1000 dilution.

Polyclonal virus culture and sequencing: Starting from a single clone of a therapeutic virus with a polytope encoding 20 neoantigens separated by a flexible spacer, a diversity library is constructed in an AdV virus in which each clone will have at least one random mutation in at least one amino acid position. A first sample of the library is retained for sequencing. The viral expression library is then propagated in E.C7 cells, and virus samples are withdrawn at different time points (e.g., 6 hrs, 12 hrs, 18 hrs, 24 hrs., etc.) and upon conclusion of virus production, a final virus sample is withdrawn. Nucleic acids are then isolated from each of the samples, yielding a mixed nucleic acid population that is representative of the library members. So prepared nucleic acid is then sequenced and the sequencing data are subjected to analysis, preferably using synchronous incremental alignment, for example, as described in our co-pending patent applications with publication numbers WO 2020/028862 (PANBAM: BAMBAM Across Multiple Organisms In Parallel) and WO 2019/236842 (Difference-Based Genomic Identity Scores). The base call fractions are then determined for each base position and a change in the population can be identified. For example, where a single viral clone has lower rate of replication due to a specific base in a specific position, the allele fraction for that base will reduce over time. Likewise, where a single viral clone has higher rate of replication due to a specific base in a specific position (e.g., leading to reduced toxicity), the allele fraction for that base will increase over time.

Of course, it should be appreciated that the analysis is not necessarily limited to observations of specific bases and direct toxicity, but may also include a secondary analysis. For example, a change in a single amino acid may result in a different spatial conformation (folding), a change in net charge, a change in secondary structure, a change in lipophilicity, etc., and all of such changes may be included in any machine learning algorithm. Therefore, and viewed from a different perspective, it should be appreciated that one or more toxicity parameters (e.g., reduced host cell growth, increased stress response in host cell, death of host cell, reduced or slowed down virus production in the host cell, mutations in viral nucleic acid, and especially in the recombinant payload (e.g., deletions, nonsense or missense mutations), reduced viral titer, etc.) can be correlated not only with a linear peptide sequence, but also with secondary aspects of that linear peptide sequence. Most typically, such secondary aspects include folding patterns and/or misfolding of an expressed polypeptide, specific secondary structures of an expressed polypeptide, domains of polarity, charge, hydrophobicity, hydrophilicity, and/or aggregation of the expressed polypeptide, specific length of the expressed polypeptide, etc.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the cells or exosomes are administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of determining payload toxicity of an expressed polypeptide in a cell, comprising:

generating or procuring a plurality of expression vectors, each containing a different recombinant nucleic acid sequence that encodes a corresponding recombinant polypeptide;

expressing the recombinant nucleic acid sequence in a plurality of host cells while culturing the host cells;

sequencing the plurality of expression vectors after culturing the host cells; and correlating at least portions of the recombinant nucleic acid sequence with a toxicity measure.

2. The method of claim 1, wherein the expression vectors are viral expression vectors.

3. The method of claim 1, wherein the expression vectors are recombinant genomes of respective therapeutic viruses.

4. The method of claim 1, wherein the recombinant polypeptide is a polytope comprising a plurality of neoantigens.

5. The method of claim 4, wherein at least two of the neoantigens are separated by a linker peptide.

6. The method of claim 4, wherein each of the plurality of the neoantigens have a length of between 8-50 amino acids.

7. The method of claim 4, wherein the polytope has at least 200 amino acids.

8. The method of claim 1, wherein the recombinant nucleic acid sequence is monoclonally expressed in the plurality of host cells.

9. The method of claim 1, wherein the recombinant nucleic acid sequence is polyclonally expressed in the plurality of host cells.

10. The method of claim 1, wherein the plurality of expression vectors are individually sequenced.

11. The method of claim 1, wherein the plurality of expression vectors are sequenced in a mixture of expression vectors.

12. The method of claim 1, wherein the toxicity measure is observed in the host cells.

13. The method of claim 12, wherein the toxicity measure in the host cells is cell death, cell stress, reduced cell division, and reduced virus production.

14. The method of claim 1, wherein the toxicity measure is observed in the recombinant nucleic acid sequence of the virus.

15. The method of claim 14, wherein the toxicity measure in the recombinant nucleic acid sequence of the virus is a nonsense mutation, a missense mutation, and a deletion.

16. The method of claim 1, wherein the step of correlating uses machine learning.

17. The method of claim 16, wherein the machine learning uses a classifier selected from the group consisting of a linear classifier, an NMF (Non-negative Matrix Factorization)-based classifier, a graphical-based classifier, a tree-based classifier, a Bayesian-based classifier, a rules-based classifier, a net-based classifier, and a kNN (k-nearest neighbor) classifier.

18. The method of claim 16, wherein the machine learning uses an autoencoder.

19. The method of claim 16, wherein the machine learning uses a secondary aspect of the recombinant polypeptide.

20. The method of claim 19, wherein the secondary aspect is a folding pattern of the polypeptide, a secondary structure of the polypeptide, a polarity domain, a charged domain, a hydrophobic domain, a hydrophilic domain, and/or aggregation of the polypeptide.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: RPL19 FORWARD

<400> SEQUENCE: 1

atgtatcaca gcctgtacct g                                              21


<210> SEQ ID NO 2
<211> LENGTH: 21
<212> TYPE: DNA
<213> ORGANISM: Artificial Sequence
<220> FEATURE:
<223> OTHER INFORMATION: RPL19 REVERSE

<400> SEQUENCE: 2

ttcttggtct cttcctcctt g                                              21


<210> SEQ ID NO 3
<211> LENGTH: 21
<212> TYPE: DNA
<213> ORGANISM: Artificial Sequence
<220> FEATURE:
<223> OTHER INFORMATION: BiP/GRP78 FORWARD

<400> SEQUENCE: 3

cgggcaaaga tgtcaggaaa g                                              21


<210> SEQ ID NO 4
<211> LENGTH: 24
<212> TYPE: DNA
<213> ORGANISM: Artificial Sequence
<220> FEATURE:
<223> OTHER INFORMATION: BiP/GRP78 REVERSE

<400> SEQUENCE: 4

ttctggacgg gcttcatagt agac                                           24


<210> SEQ ID NO 5
<211> LENGTH: 22
<212> TYPE: DNA
<213> ORGANISM: Artificial Sequence
<220> FEATURE:
<223> OTHER INFORMATION: CHOP FORWARD

<400> SEQUENCE: 5

accaagggag aaccaggaaa cg                                             22


<210> SEQ ID NO 6
<211> LENGTH: 22
<212> TYPE: DNA
<213> ORGANISM: Artificial Sequence
<220> FEATURE:
<223> OTHER INFORMATION: CHOP REVERSE

<400> SEQUENCE: 6
```

-continued

```
tcaccattcg gtcaatcaga gc                                             22


<210> SEQ ID NO 7
<211> LENGTH: 21
<212> TYPE: DNA
<213> ORGANISM: Artificial Sequence
<220> FEATURE:
<223> OTHER INFORMATION: XBP1 FORWARD

<400> SEQUENCE: 7

ttacgagaga aaactcatgg c                                              21


<210> SEQ ID NO 8
<211> LENGTH: 22
<212> TYPE: DNA
<213> ORGANISM: Artificial Sequence
<220> FEATURE:
<223> OTHER INFORMATION: XBP1 REVERSE

<400> SEQUENCE: 8

gggtccaagt tgtccagaat gc                                             22
```